United States Patent
Zeng

(10) Patent No.: US 9,664,672 B2
(45) Date of Patent: May 30, 2017

(54) DRY CHEMICAL TEST STRIP WITH MULTIPLE LAYERS OF MEMBRANES BASED ON CONCENTRATION GRADIENT

(71) Applicant: Rongbin Zeng, Nanjing (CN)

(72) Inventor: Rongbin Zeng, Nanjing (CN)

( * ) Notice: Subject to any disclaimer, the term of this patent is extended or adjusted under 35 U.S.C. 154(b) by 0 days.

(21) Appl. No.: 15/307,009

(22) PCT Filed: Feb. 28, 2015

(86) PCT No.: PCT/CN2015/073387
§ 371 (c)(1),
(2) Date: Oct. 27, 2016

(87) PCT Pub. No.: WO2016/134531
PCT Pub. Date: Sep. 1, 2016

(65) Prior Publication Data
US 2017/0074865 A1    Mar. 16, 2017

(51) Int. Cl.
*A61L 2/08* (2006.01)
*G01N 33/52* (2006.01)
*G01N 33/00* (2006.01)

(52) U.S. Cl.
CPC .......... *G01N 33/525* (2013.01); *G01N 33/00* (2013.01); *G01N 2333/904* (2013.01); *G01N 2333/90283* (2013.01); *G01N 2333/916* (2013.01); *G01N 2333/91074* (2013.01)

(58) Field of Classification Search
CPC ................. G01N 33/525; G01N 33/00; G01N 2333/91074; G01N 2333/904; G01N 2333/90283; G01N 2333/916
See application file for complete search history.

(56) References Cited

U.S. PATENT DOCUMENTS

| | | | |
|---|---|---|---|
| 4,604,264 A | 8/1986 | Rothe et al. | |
| 4,778,758 A | 10/1988 | Ericsson et al. | |
| 5,508,173 A | 4/1996 | Amano et al. | |
| 5,744,096 A * | 4/1998 | Jones | B01L 3/5023 422/412 |

(Continued)

FOREIGN PATENT DOCUMENTS

| CN | 1225450 A | 8/1999 |
|---|---|---|
| CN | 2462387 Y | 11/2001 |

(Continued)

*Primary Examiner* — Dennis M White
(74) *Attorney, Agent, or Firm* — Gokalp Bayramoglu

(57) ABSTRACT

A dry chemical test strip with multiple layers of membranes based on concentration gradient, comprising a substrate, an indicator layer, a reagent layer and a diffusion layer, further comprises a concentration gradient layer. Wherein a first reagent is uniformly applied on the reagent layer, a second reagent is applied on the concentration gradient layer. The concentration gradient increment $\nabla\rho$ of the second reagent is 0 in the width direction of the test strip, and is a constant or a function of the variable of length in the length direction of the test strip, a chromogenic reagent is uniformly applied on the indicator layer. The dry chemical test strip with multiple layers of membranes based on concentration gradient can allow all the testing and analysis procedures to be directly carried out on the test strip, test results to be directly obtained on the spot without the help of instruments.

10 Claims, 3 Drawing Sheets

(56) References Cited

U.S. PATENT DOCUMENTS

2013/0244316 A1   9/2013  Brocco

FOREIGN PATENT DOCUMENTS

| CN | 2564584 Y | 8/2003 |
| CN | 1667414 A | 9/2005 |
| CN | 1888900 A | 1/2007 |
| CN | 201309942 Y | 9/2009 |
| CN | 101592656 A | 12/2009 |
| CN | 101762628 A | 6/2010 |
| CN | 102323399 A | 1/2012 |

* cited by examiner

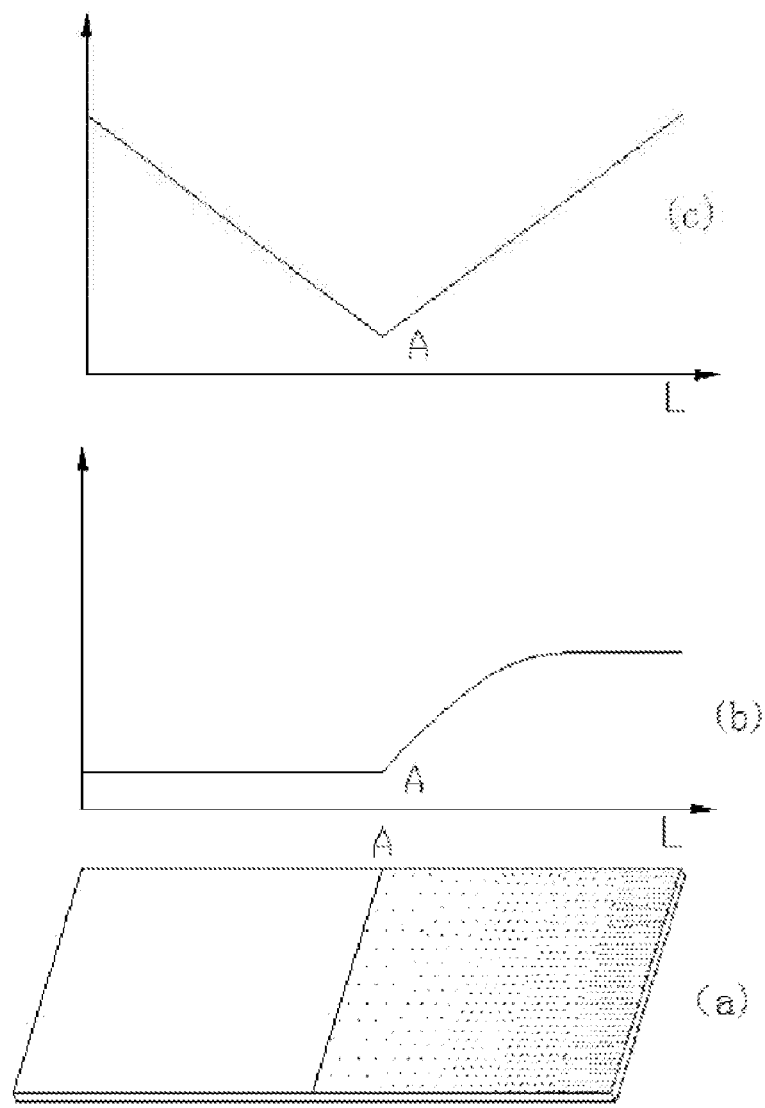
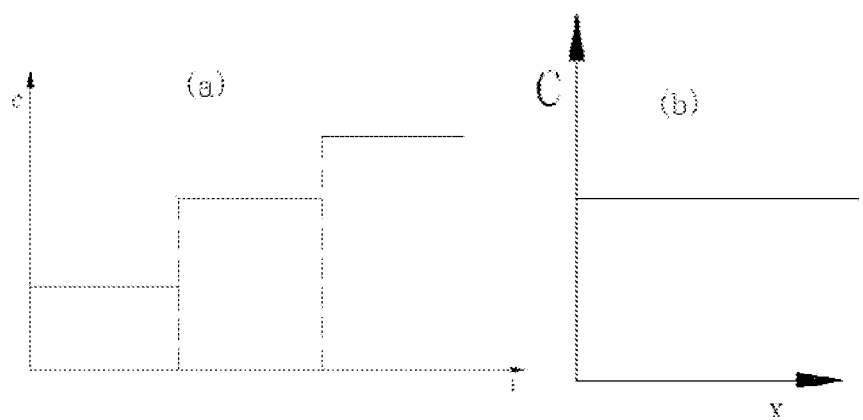
Fig. 3
Fig. 4

DRY CHEMICAL TEST STRIP WITH MULTIPLE LAYERS OF MEMBRANES BASED ON CONCENTRATION GRADIENT

CROSS REFERENCE TO RELATED APPLICATIONS

This application is the national phase entry of International Application No. PCT/CN2015/073387, filed on Feb. 28, 2015, the entire contents of which are incorporated herein by reference.

TECHNICAL FIELD

The invention relates to a chemical test product, particularly relates to a dry chemical test strip with multiple layers of membranes based on concentration gradient, which is used for a rapid quantitative testing on site.

BACKGROUND

With an improvement in living standards, people care more and more about their health, safety and living conditions, which relies on analysis and tests, including medical clinical testing, food safety testing, environmental quality testing, etc. Those testing methods of chemical analysis and biochemical analysis are developed from the previous manual experimental methods to automatic analysis tests by means of automatic analytical instruments and on-site tests (e.g. POCT, point of care testing), greatly reducing the workload of the analysis operators. According to the analysis reagent types, the analysis tests can be divided into two methods: tests by means of liquid reagent and dry chemical reagent. By using the method of the liquid reagent (the wet chemistry), a sufficient accuracy and precision can be obtained, but it requires expensive instruments and professional personnel. In addition, it needs complicated operations and cannot obtain results quickly, which is not suitable for on-site tests (e.g. the demands for testing in hospital emergency rooms, and a small quantity of samples for tests). By contrast, the method of the dry chemical reagent has advantages in easy operation, rapid measurement, flexibility and no need for professional personnel which remedies the deficiencies of the wet chemistry well. The accuracy and precision of the dry chemical reagent are close to the testing method of the wet chemistry. Particularly, the dry chemical test-strip (paper), used in the dry chemistry, is widely used in the fields of medical clinical testing, food safety testing, and environmental quality testing, offering a great convenience. Relative to the traditional "wet chemistry" (i.e., solution chemistry), the "dry chemistry" is a method that the substance to be tested directly reacts with the dry reagent powder solidified on the carrier, with the liquid in the tested samples serving as a reaction medium. The greatest difference between the dry chemistry and the traditional wet chemistry lies with the different media involved in the chemical reactions. With the developments of separation, purification and storage of enzymes of biochemistry, and an advancement in the technology of sensors, photometers and electrodes, as well as the popularity of computer applications, the dry chemical technology has made a great progress in the past 20 years. The dry chemical test strip (paper) is now widely used in fields of medical clinical testing, food safety testing, and environmental quality testing, for which the methods of electrochemistry and colorimetry are commonly used.

The electrochemistry, as described in CN101762628A, entitled "Dry enzyme method biochip/test strip", is made with the dry enzyme work electrode, the reference electrode, the testing liquid diffusing reticular membrane, the hydrophobic insulation paint on the PET substrate, and the testing result signals need to be read by electrochemical instruments.

The dry chemical test strip of colorimetry developed earlier, from the initial one-layer structure to two-layer structure, three-layer structure and the latest multilayer structure.

The initial one-layer structure, such as the pH strip for testing the acidity and alkalinity and the potassium-iodide-starch test strip for measuring oxides, both are mainly used in qualitative experiments, with semi-quantitative values at most.

The simplest reagent carrier for the biochemistry analysis, developed on the basis of the one-layer structure, is the two-layer structure. A cellulose sheet of the reagent layer is provided on the supporting layer, i.e., plastic substrate, with all the reagents having a pre-solid phase in the cellulose sheet. The urine biochemical analysis reagent strip is a common two-layer structure, as described in CN1888900A, entitled "PH Sectional sequencing 13 item urine test paper". The thirteen test items are assigned to thirteen different reagent strips affixed on the plastic substrate. The composition of urine to be measured reacts directly with the reagents having a pre-solid phase in fee cellulose sheet to calculate the concentration of the composition to be measured by measuring color intensity changes through the reflection photometer. This structure can only be used for qualitative or semi-quantitative measurements, and the result of this strip also needs to be read by an instrument, with a narrow linear range of the measurement. Experimental results will be impacted in a circumstance of drug involvement, which limits its applications in other quantitative fields.

A porous membrane filtration layer is added on the reagent layer to form a three-layer structure membrane. The function of porous membrane filtration layer is to filter out impurities in the samples, protecting the reagent layer. The reagent strip for measuring glucose by micro method is a common three-layer structure. The optical measuring path of the reagent carrier in the three-layer structure is implemented by using the transparent plastic substrate, rather than passing through the top filter layer. As a result, the influence of the interfering composition in the samples is eliminated to ensure the stability and accuracy of the composition to be measured. For example, colorimetric blood glucose test strip preparing and supporting instruments are disclosed in CN1225450A, entitled "Test paper and analyte measuring tip".

There is only one reagent layer in the three-layer structure. However, there are many analytical tests in which all the reagents cannot be mixed in advance, while some complex testing solution needs to be preheated, which limits the application fields of the dry chemical test strip (paper) with the three-layer structure. In order to overcome the defects of the three-layer structure, the current latest technology—a multilayer film method, i.e., multiple layers of membranes reagent carrier of the dry chemistry is provided. The multilayer film method can mainly be divided into longitudinal method and transverse method, according to the fabrication process. The first method is a multilayer film dry method, which is represented by Johnson & Johnson and Fujifilm corporations, applying the reagent layer, the auxiliary reagent layer, the light diffusing layer, the distributing layer and other reagents on the transparent support layer using coating technology of photographic film, so as to measure the optical density changes from the opposite side of the support layer, as disclosed in U.S. Pat. No. 5,508,173. The second method relates to the dry chemistry products of Roche as disclosed in U.S. Pat. No. 4,604,264, applying the reagent on the multi-silk fiber or fabric, contacting and reacting with the upper reagent layer after whole blood passing through the glass fiber for being filtered transversely; and then measuring the optical density changes by the transparent film which covers at the top.

Those dry chemical test strips (paper) described above are difficult to be quantitative. Further, some of the test strips have a complicated production process, and high requirements for materials and equipment. Some of them may cause some defects, such as a few bubbles and excess liquid, etc. easily generated at the sample adding end, causing possible interferences to the samples when the samples are added and measured on the same side, and temperature and time controls required for some testing items. Furthermore, the current dry biochemical analyzer is a large-scale equipment, with all the biochemical testing items integrated in a single machine, such as VITROS series of Johnson & Johnson (VITR0S-25, VITR0S-950), a semi-automatic and fully automatic dry biochemical analyzer and biochemical reagent, wherein VITR0S-250 and VITR0S-950 are mainly used in hospitals, and it is inconvenient to start the machine in case of only few samples. In case of emergencies on site such as, acute abdomen, an immediate test is urgently needed, and the quantitative test strip can meet the instant needs, which is of great significance for on-site testing.

In order to realize the rapid and accurate quantitative measurements and analysis on site, the sample liquid, is rapidly tested quantitatively on site, by artificial controls of the concentration distribution of reagent on the dry chemical test strip (paper). The liquid to be tested is realized to be diffused and permeated in the strip (paper), similar to the principle of chemical titration.

The method of CN2564584, entitled "Detecting plate of bacterial medicine sensitivity experiment for detecting minimum bacterium-inhibiting concentration of antibiotics" is using many different quantitative lands of antibiotic concentration gradient filter membrane strips fixed on the substrate. The feature is that the concentration of antibiotic on the plastic carrier exponentially and discontinuously decreases in the longitudinal direction, with the same concentration gradient method as the transverse direction (as shown in FIG. 5).

The method of CN201309942, entitled "Comb-shaped medicament susceptibility test scrip" is somewhat similar to the method of CN2564584. The feature is that the concentration of antibiotic on the comb teeth of the plastic carrier exponentially and discontinuously decreases in the longitudinal direction, with the concentration in the transverse direction (as shown in FIG. 6).

The method of CN1667414, entitled "Stepped concentration gradient detecting bar and preparing process thereof" is that the earner is divided into a plurality of equal areas on the same side of the carrier and the drag blocks having the set shape and area are applied symmetrically at the centers of each equal area. The dosage of each drug block changes with gradients of one or more segments, i.e. the drag blocks in different segments have different concentrations. But each drag block in the same segment has the same coating thickness and concentration. The size of each drug block increases or decreases sequentially with gradient, characterized in that the distribution of the concentration gradient is determined by the areas of the antibiotic agent coated on the substrate i.e., the concentration of the antibiotic agent is presented with a discontinuous gradient distribution longitudinally in the strip (paper) (as shown in FIG. 8), while the concentration of antibiotic agent is presented with a peak distribution transversely in the strip (paper) (as shown in FIG. 7). This method is also used in U.S. patent applications US20130244316A1, entitled "Paper strip for determining minimum inhibitory concentrations of antibiotics" and U.S. Pat. No. 4,778,758"Device for susceptibility testing of microorganisms".

The patents as above realize the gradient distribution of antibiotic agent, mainly applied in the microbial drug sensitivity test, which is a test of microbial resistance. The distribution of the concentration of the antibiotic agent changing with gradient is formed on the medium surface by diffusing the antibiotic in the medium during the process of the experiment. The bacterial minimum inhibitory concentration (MIC value, Minimal inhibitory concentration) can then be read after cultivation, and thus the result cannot be rapidly obtained on site.

SUMMARY OF THE INVENTION

In view of the deficiencies of the prior art, the purpose of the present invention is to provide a dry chemical test strip with multiple layers of membranes based on concentration gradient, which can be used for rapid quantitative tests on the spot, and has a continuous stepless change in concentration.

To achieve the above purpose, the technical solutions of the invention are provided:

The invention discloses a dry chemical test strip with multiple layers of membranes based on concentration gradient, comprising a substrate, an indicator layer, a reagent layer and a diffusion layer, which are arranged successively from bottom to top, characterized in that, the test strip further comprises a concentration gradient layer, which is arranged on the upper or the lower surface of the reagent layer. Wherein a first reagent is uniformly applied on the reagent layer, and a second reagent is applied on the concentration gradient layer. The concentration gradient increment $\nabla\rho$ of the second reagent is 0 in the width direction of the test strip, and is a constant or a function of the variable of length in the length direction of the test strip. A chromogenic reagent is uniformly applied on the indicator layer.

The concentration gradient layer is any one of polyvinyl alcohol, gelatin and a mixture of polyvinyl alcohol and gelatin.

The concentration gradient layer is a porous coating or a prefabricated porous membrane.

The diffusion layer is a hydrophilic membrane.

A siphon structure is provided on the hydrophilic membrane.

The reagent layer is made of a high molecular polymer material.

The reagent layer is a porous coating or a prefabricated porous membrane.

The indicator layer is made of a high molecular polymer material.

The indicator layer is a porous coating or a prefabricated porous membrane

The substrate is made of a transparent material, having a thickness of 0.1-0.3 mm.

A ruler is provided on the lower surface of the substrate.

Compared with the prior art, the invention has the advantages:

The dry chemical test strip with multiple layers of membranes based on concentration gradient includes a concentration gradient layer, as a result the concentration distribution of the reagent is presented with a continuous stepless change on the test strip. All the testing and analysis processes can be carried out directly on the test strip. Furthermore, the testing results can be obtained without the help of an instrument on the spot. At the same time, the testing process is not limited by the temperature and the time, which can be easily operated. The testing means is open and can be operated without any special training, which is suitable for on-site inspections of professionals and non-professionals.

BRIEF DESCRIPTION OF THE DRAWINGS

FIG. 3 is a test result diagram of the dry chemical test strip of the invention.

FIG. 4 is a distribution diagram of the antibiotic concentration on the testing plate for measuring the bacterial minimum inhibitory concentration of antibiotics in the bacterial medicine sensitivity experiment of the prior art.

In figures: 1. substrate; 2. indicator layer; 3. reagent layer; 4. concentration gradient layer; 5. diffusion layer.

DETAILED DESCRIPTION OF THE EMBODIMENTS

The invention is further illustrated with the accompanying drawings:

Embodiment 1

Figure 1:
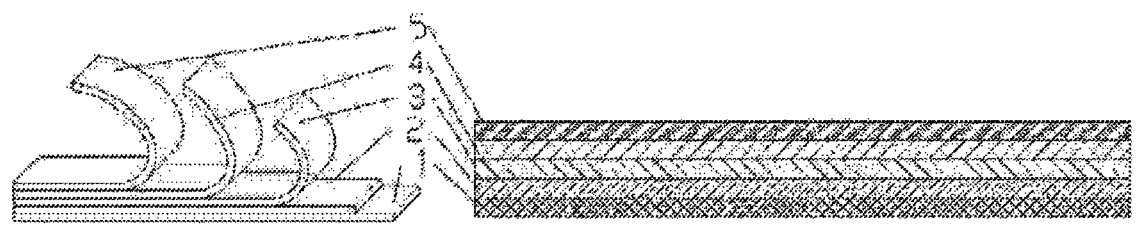
FIG. 1 is a structural schematic diagram of the dry chemical test strip of the invention.
Figure 2:
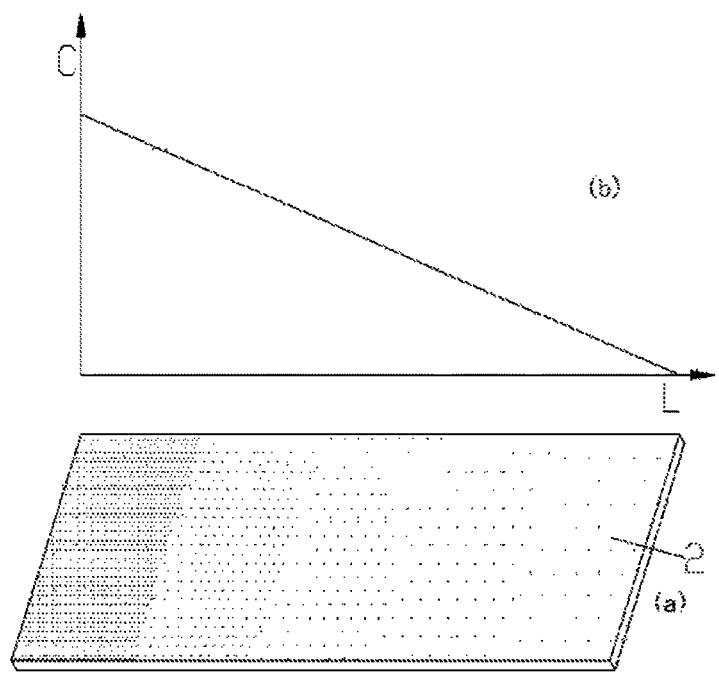
FIG. 2 is a reagent distribution diagram of the concentration gradient layer of the invention.
Figure 5:
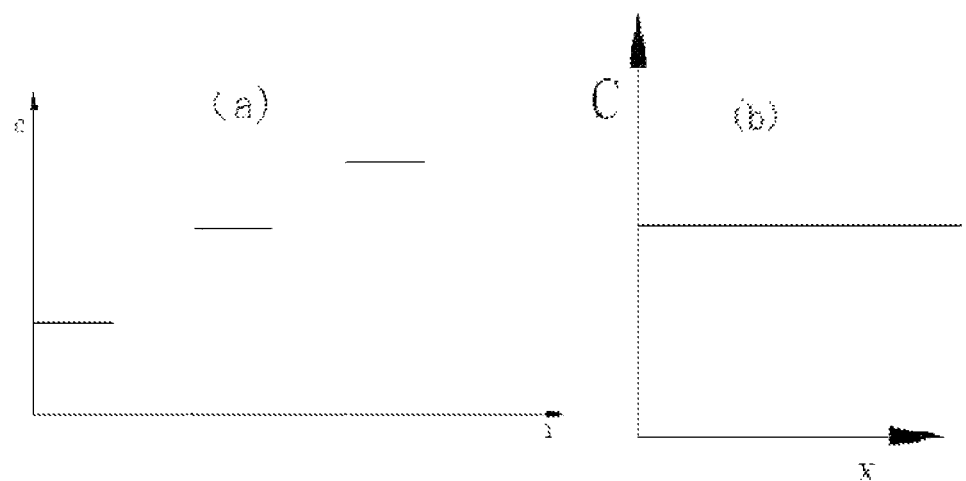
FIG. 5 is an antibiotic distribution diagram of the comb-shaped medicine sensitivity test strip in the prior art.
Figure 6:
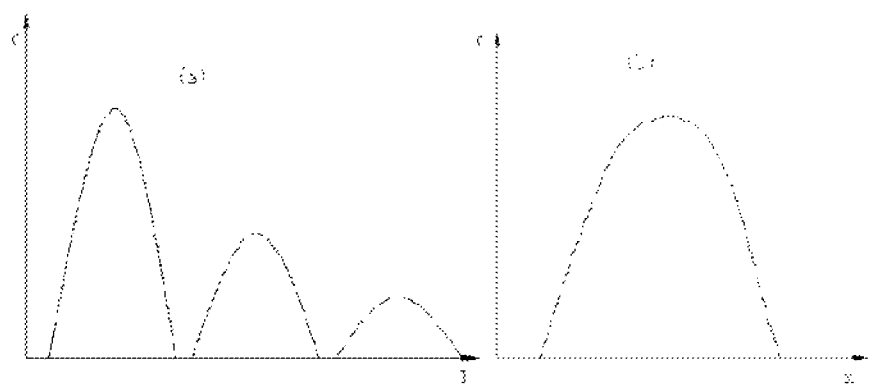
FIG. 6 is an antibiotic distribution diagram of a stepped concentration gradient test strip in the prior art.
Figure 7:
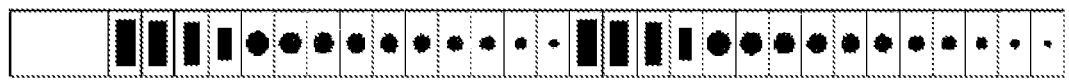
FIG. 7 is an antibiotic coating diagram of a stepped concentration gradient test strip in the prior art.
Figure 8:
FIG. 8 is a diagram of a ruler on the lower surface of the substrate of the invention.

As shown in FIG. 1, FIG. 3 and FIG. 8, the preparation method for the water hardness test strip (paper) based on concentration gradient, used for rapid measurement of the water hardness index from different sources, is disclosed. The water hardness test strip (paper) is prepared with two different structures and methods. The strip (paper) is composed of five basic functional layers, which are substrate 1, indicator layer 2, reagent layer 3, concentration gradient layer 4 and diffusion layer 5. The first preparation method is provided as follows: The top layer of the test strip is diffusion layer 5, which is made of the hydrophilic porous cellulose membrane formed by coating. The multilayer structure is prepared by layer coating. Reagent layer 3 is located under diffusion layer 5, and reagent layer 3 is made of porous polyvinyl alcohol. The reaction solution made of three hydroxy methyl amino methane (tris) 10-15 g/L, is coated to prepare the reagent layer. The polyvinyl alcohol emulsion is mixed with the reagent solution in the proportion of 1:1~4:1. Concentration gradient layer 4 is located under reagent layer 3, and concentration gradient layer 4 is made of porous polyvinyl alcohol material. A porous membrane is first formed by uniformly coating the polyvinyl alcohol material, then the ethylenediaminetetraacetic acid (EDTA) is coated as a complexing agent on the polyvinyl alcohol porous membrane in a concentration gradient linearly decreasing manner or a concentration gradient stepped decreasing manner, to prepare concentration gradient layer 4. Indicator layer 2 is located under concentration gradient layer 4, and the indicator layer 2 is made of porous polyvinyl alcohol material. The chromogenic agent of indicator layer 2 is acid chrome blue K 1-2 g/L. Substrate 1 is located under indicator layer 2, and the substrate is made of the grass green transparent PET sheet or the polycarbonate sheet, having a thickness of 0.15-0.2 mm. The second preparation method is provided as follows: diffusion layer 5 is made of hydrophilic nylon membrane, and the multilayer structure is prepared by the current multilayer film lamination method. Reagent layer 3 is located under the diffusion layer 5, and is made by doing the finished polyvinyl alcohol porous membrane away from the light, after being dipped in the reagent solution for 5 minutes. Concentration gradient layer 4 is located under the reagent layer 3, and is made by coating ethylenediaminetetraacetic acid (EDTA) on the finished polyvinyl alcohol porous membrane in a concentration gradient linearly decreasing manner. Indicator layer 2 is located under concentration gradient layer 4, and is made by drying the finished polyvinyl alcohol porous membrane, away from the light, after being dipped in the chromogenic agent for 5 minutes. The substrate is located under indicator layer 2, and is made of the grass green transparent PET sheet or the polycarbonate sheet, having a thickness of 0.15-0.2 mm. Each layer is sequentially pressed and fixed on the substrate by the nylon membrane of diffusion layer 5. When measuring the total water hardness, the water hardness test strip (paper) is prepared by the first preparation method of multilayer film and the sampling is achieved by adding a certain amount of test solution to diffusion layer 5. The water hardness test strip (paper) can also be prepared by the second preparation method of multilayer film, and the sampling is achieved by rapidly putting the strip (paper) into the test solution and then taking it out within 3 seconds, followed by blotting the water drops from the strip. Left to rest for 3 minutes after sampling, the water hardness test strip (paper) is observed for the result. The concentration gradient layer or the reagent layer of the water hardness test strip (paper), which is close to the substrate, is presented with a red-purple (boundary A)-blue purple transition. Due to the light absorption effect by the glass green transparent substrate, a brick red-blue purple (boundary A)-blue transition is presented from the perspective of the substrate. The value of A is read using the ruler, as shown in (a) of FIG. 3. Alternatively, the similar scanning curve as shown in (c) of FIG. 3 is obtained by the color scanning, and then the value of the inflection point A is read.

Embodiment 2

As shown in FIG. 1, FIG. 3 and FIG. 8, the preparation method for the acid value test strip (paper) based on concentration gradient, used for rapid measurement of the acid value index, is disclosed. The acid value test strip (paper) is prepared with two different structures and methods. The strip (paper) is composed of five basic functional layers, which are substrate 1, indicator layer 2, reagent layer 3, concentration gradient layer 4 and diffusion layer 5. The first preparation method is provided as follows: The top layer of the test strip is diffusion layer 5, which is made of the porous cellulose membrane formed by coating. The multilayer structure is prepared by layer coating. Reagent layer 3 is located under diffusion layer 5, and reagent layer 3 is made of porous polyvinyl alcohol. The reaction solution made of protective agent KD 2-4 g/L is coated to prepare the reagent layer. The polyvinyl alcohol emulsion is mixed with reagent solution in the proportion of 1:1~4:1. Concentration gradient layer 4 is located under reagent layer 3, and concentration gradient layer 4 is made of porous polyvinyl alcohol material. A porous membrane is first formed by uniformly coating the mixture of polyvinyl alcohol material and the protective agent, then the potassium hydroxide as the titrant is coated on the polyvinyl alcohol porous membrane in a concentration gradient linearly decreasing manner or a concentration gradient stepped decreasing manner, to prepare concentration gradient layer 4. Indicator layer 2 is located under concentration gradient layer 4, and the indicator layer 2 is made of porous polyvinyl alcohol material. The chromogenic agent of indicator layer 2 is phenolphthalein 1-2 g/L. Substrate 1 is located under indicator layer 2, and the substrate is made of the colorless transparent PET sheet or the polycarbonate sheet, having a thickness of 0.15-0.2 mm. The second preparation method is provided as follows: diffusion layer 5 is made of hydrophilic nylon membrane, and the multilayer structure is prepared by the current multilayer film lamination method. Reagent layer 3 is located under the diffusion layer 5, and is made by drying the finished polyvinyl alcohol porous membrane away from the light, after being dipped in the reagent solution for 5 minutes. Concentration gradient layer 4 is located under the reagent layer 3, and is made by coating potassium hydroxide as the titrant on the finished polyvinyl alcohol porous membrane in a concentration gradient linearly decreasing manner. Indicator layer 2 is located under concentration gradient layer 4, and is made by drying the finished polyvinyl alcohol porous membrane, away from the light, after being dipped in the chromogenic agent for 5 minutes. The substrate located under indicator layer 2, is made of the colorless transparent PET sheet or the polycarbonate sheet, having a thickness of 0.15-0.2 mm. Each layer is sequentially pressed and fixed on the substrate by the nylon membrane of diffusion layer 5. When measuring the acid value of grease, the acid value test strip (paper) is prepared by the first preparation method of multilayer film and the sampling is achieved by adding a certain amount of processed test solution to diffusion layer 5. The acid value test strip (paper) can also be prepared by the second preparation method of multilayer film, and the sampling is achieved by rapidly putting the strip (paper) into the test solution and then taking it out within 3 seconds, followed by blotting the liquid drops from the strip. Left to rest for 3 minutes after sampling, the acid value test strip (paper) is observed for the result. The acid value test strip (paper) is presented with a no color—light red (boundary A)—red transition. The value of A is read using the ruler, as shown in (a) of FIG. 3. Alternatively, the similar scanning curve as shown in (b) of FIG. 3 is obtained by the color scanning, and then the value of the inflection point A is read.

Embodiment 3

As shown in FIG. 1, FIG. 3 and FIG. 8, the preparation method for the blood sugar test strip (paper) based on concentration gradient, used for rapid measurement of the glucose in the blood for clinical trials, is disclosed. The strip (paper) is composed of five basic functional layers, which are substrate 1, indicator layer 2, reagent layer 3, concentration gradient layer 4 and diffusion layer 5. The multilayer structure is prepared by layer coating. The top layer of the test strip is diffusion layer 5, which is made of the porous cellulose membrane formed by coating. Reagent layer 3 is located under diffusion layer 5, and reagent layer 3 is made of a porous membrane formed by polyvinylpyrrolidone and polysulfone material and the porous membrane made of polysulfone material is also used for adsorbing and removing the blood cells. The reaction solution made of a mixture of 10 IU/L glucose oxidase, 0.038 mol/L citric acid, 0.126 mol/L disodium hydrogen phosphate, 10 g/L trehalose, 5 g/L glycine, 3 g/L BSA, and 10 g/L PEG4000, is coated on the porous membrane to prepare the reagent layer. Concentration gradient layer 4 is located under reagent layer 3, and concentration gradient layer 4 is made of porous polyvinyl alcohol material. A porous membrane is first formed by uniformly coating the polyvinyl alcohol material, the antioxidants (BHT) is second coated on the polyvinyl alcohol porous membrane in a concentration gradient linearly decreasing manner or a concentration gradient stepped decreasing manner, and then the reaction solution made of a mixture of 20 UI/L horseradish peroxidase, 0.037 mol/L citric acid, 0.126 mol/L disodium hydrogen phosphate, 10 g/L trehalose, 5 g/L glycine, 3 g/L BSA and 10 g/L PEG4000 is coated on the polyvinyl alcohol porous membrane to prepare concentration gradient layer 4. Indicator layer 2 is located under concentration gradient layer 4, and the indicator layer 2 is made of porous polyvinyl alcohol material. The chromogenic agent of indicator layer 2 is 1-2 g/L TMB. Substrate 1 is located under indicator layer 2, and the substrate is made of tire colorless transparent PET sheet or the polycarbonate sheet, having a thickness of 0.15-0.2 mm. When measuring the blood sugar, the sampling is achieved by adding a certain amount of blood to diffusion layer 5. Left to rest for 3 minutes after sampling, the blood sugar test strip (paper) is observed for the result. The blood sugar test strip (paper) is presented with a no color—blue transition, with the visible color boundary A. The value of A is read using the ruler, as shown in (a) of FIG. 3. Alternatively, the similar scanning curve as shown in (b) of FIG. 3 is obtained by the color scanning, and then the value of the inflection point A is read.

Embodiment 4

As shown in FIG. 1, FIG. 3 and FIG. 8, the preparation method for the glutamic pyruvic transaminase test strip (paper) based on concentration gradient, used for rapid measurement of content of glutamic pyruvic transaminase in the blood for clinical trials, is disclosed. The strip (paper) is composed of five basic functional layers, which are substrate 1, indicator layer 2, reagent layer 3, concentration gradient layer 4 and diffusion layer 5. The multilayer structure is prepared by layer coating. The top layer of the test strip is diffusion layer 5, which is made of the hydrophilic porous cellulose membrane formed by coating. Concentration gradient layer 4 is located under diffusion layer 5, and is made of porous polyvinyl alcohol material. The glutamic pyruvic transaminase inhibitors (GBH) is coated on the polyvinyl alcohol porous membrane in a concentration gradient linearly decreasing manner or a concentration gradient exponentially changing manner, and then the reaction solution made of a mixture of Good's buffer: 200 mM, MgCl2*6H2 0:2 g/L, KH2PO4:20 mM and trehalose: 0.5% is coated to prepare concentration gradient layer 4. Reagent layer 3 is located under concentration gradient layer 4, and is made of polyvinyl alcohol. The porous membrane is first formed by coating polyvinyl alcohol material, and then the reaction solution made of a mixture of alanine: 1000α A-Ketoglutaric Acid Disodium: 20 mM, peroxidase: 100 U/ml, pyruvate oxidase 100 U/ml, flavin adenine dinucleotide (FAD): 0.2 mg/ml, thiamine pyrophosphate (TPP): 0.8 mg/ml and TMB: 0.1% is coated to prepare reagent layer 3. Indicator layer 2 is located under reagent layer 3, and indicator layer 2 is made of porous polyvinyl alcohol material. The chromogenic agent of indicator layer 2 is 1.0 g/L TMB. Substrate 1 is located under indicator layer 2, and the substrate is made of the colorless transparent PET sheet or the polycarbonate sheet, having a thickness of 0.15-0.2 mm. When measuring the content of glutamic pyruvic transaminase in the blood, the sampling is achieved by adding a certain amount of test solution to diffusion layer 5. Left to rest for 30 minutes after sampling, the glutamic pyruvic transaminase test strip (paper) is observed for the result. The glutamic pyruvic transaminase test strip (paper) is presented with a no color—blue transition, with the visible color boundary A. The value of A is read using the ruler, as shown in (a) of FIG. 3. Alternatively, the similar scanning curve as shown in (b) of FIG. 3 is obtained by the color scanning, and then the value of the inflection point A is read.

Embodiment 5

As shown in FIG. 1, FIG. 3 and FIG. 8, the preparation method for the bone alkaline phosphatase test strip (paper) based on concentration gradient, used for rapid measurement of content of bone alkaline phosphatase in the blood for clinical trials, is disclosed. The strip (paper) is composed of five basic functional layers, which are substrate 1, indicator layer 2, reagent layer 3, concentration gradient layer 4 and diffusion layer 5. The multilayer structure is prepared by layer coating. The top layer of the test strip is diffusion layer 5, which is made of the hydrophilic porous cellulose membrane formed by coating. Concentration gradient layer 4 is located under diffusion layer 5, and is made of porous polyvinyl alcohol membrane. The bone alkaline phosphatase inhibitors (BALH) is coated on the polyvinyl alcohol porous membrane in a concentration gradient linearly decreasing manner or a concentration gradient exponentially changing manner, to prepare concentration gradient layer 4. Reagent layer 3 is located under concentration gradient layer 4, and reagent layer 3 is made of polyvinyl alcohol. The porous membrane is first formed by coating polyvinyl alcohol material, and then the reaction solution made of a mixture of three hydroxy methyl amino methane (Tris): 5-10/L, lectins: UA-3:0.5%, MgCl2*6H20: 5 mmol/L and nitro blue tetrazolium chloride (NBT) 1.0 mmol is coated to prepare reagent layer 3. Indicator layer 2 is located under reagent layer 3, and indicator layer 2 is made of porous polyvinyl alcohol material. The chromogenic agent of indicator layer 2 is bromo chloro indole phosphate (BCIP) 1.0 mmol/L. Substrate 1 is located under indicator layer 2, and the substrate is made of the colorless transparent PET sheet or the polycarbonate sheet, having a thickness of 0.15-0.2 mm. When measuring the content of bone alkaline phosphatase in the blood, the sampling is achieved by adding a certain amount of blood test solution to diffusion layer 5. Left to rest for 30 minutes after sampling, the bone alkaline phosphatase test strip (paper) is observed for the result. The bone alkaline phosphatase test strip (paper) is presented with a no color—purple transition, with the visible color boundary A. The value of A is read using the ruler, as shown in (a) of FIG. 3. Alternatively the similar scanning curve as shown in (b) of FIG. 3 is obtained by tire color scanning, and then the value of the inflection point A is read.

Embodiment 6

As shown in FIG. 1, FIG. 3 and FIG. 8, the preparation method for the superoxide dismutase test strip (paper) based on concentration gradient, used for rapid measurement of the superoxide dismutase, is disclosed. The strip (paper) is composed of five basic functional layers, which are substrate 1, indicator layer 2, reagent layer 3. concentration gradient layer 4 and diffusion layer 5. The multilayer structure is prepared by layer coating. The top layer of the test strip is diffusion layer 5, which is made of the hydrophilic porous cellulose membrane formed by coating. Reagent layer 3 is located under diffusion layer 5. and reagent layer 3 is made of a porous polyvinyl alcohol membrane. The reaction solution made of a mixture of hypoxanthine:200 mM, and hydroxylamine hydrochloride: 2.0/L, is coated on the porous membrane to prepare reagent layer 3. Concentration gradient layer 4 is located under reagent layer 3, and concentration gradient layer 4 is made of porous polyvinyl alcohol material. A porous membrane is first formed by uniformly coating the polyvinyl alcohol material, the xanthine oxidase (XO) is second coated on the polyvinyl alcohol porous membrane in a concentration gradient linearly decreasing manner or a concentration gradient exponentially changing manner, and then the reaction solution made of a mixture of three hydroxy methyl amino methane (Tris): 5-10/L, trehalose: 10 g/L, glycine: 5 g/L, BSA: 3 g/L and PEG4000: 10 g/L is coated on the polyvinyl alcohol porous membrane to prepare concentration gradient layer 4. Indicator layer 2 is located under concentration gradient layer 4, and the indicator layer 2 is made of porous polyvinyl alcohol material. The chromogenic agent of indicator layer 2 is amino benzene sulfonic acid reagent: 2.0/L and a-naphthylamine: 1.0/L. Substrate 1 is located under indicator layer 2, and the substrate is made of the colorless transparent PET sheet or the polycarbonate sheet, having a thickness of 0.15-0.2 mm. When measuring the content of superoxide dismutase in the biological samples, the sampling is achieved by adding a certain amount of biological sample test solution to diffusion layer 5. Left to rest for 30 minutes after sampling, the superoxide dismutase test strip (paper) is observed for the result. The superoxide dismutase test strip (paper) is presented with a no color—purple red transition, with the visible color boundary A. The value of A is read using the ruler, as shown in (a) of FIG. 3. Alternatively, the similar scanning curve as shown in (b) of FIG. 3 is obtained by the color scanning, and then the value of the inflection point A is read.

Embodiment 7

As shown in FIG. 1, FIG. 3 and FIG. 8, the preparation method for the residual chlorine test strip (paper) based on concentration gradient, used for rapid measurement of the content of residual chlorine in different wafer samples, is disclosed. The strip (paper) is composed of five basic functional layers, which are substrate 1, indicator layer 2, reagent layer 3, concentration gradient layer 4 and diffusion layer 5. The multilayer structure is prepared by layer coating. The top layer of the test strip is diffusion layer 5, which is made of the hydrophilic porous cellulose membrane formed by coating. Concentration gradient layer 4 is located under diffusion layer 5, and is made of porous polyvinyl alcohol membrane. The antioxidant (BHT) is coated on the polyvinyl alcohol porous membrane in a concentration gradient linearly decreasing manner or a concentration gradient exponentially changing manner, to prepare concentration gradient layer 4. Reagent layer 3 is located under concentration gradient layer 4, and reagent layer 3 is made of polyvinyl alcohol. The porous membrane is first formed by coating polyvinyl alcohol material, and then the reaction solution made of KH2PO4: 20 mM is coated to prepare reagent layer 3. Indicator layer 2 is located under reagent layer 3, and indicator layer 2 is made of porous polyvinyl alcohol material. The chromogenic agent of indicator layer 2 is TMB: 0.1%. Substrate 1 is located under indicator layer 2, and the substrate is made of the colorless transparent PET sheet or the polycarbonate sheet, having a thickness of 0.15-0.2 mm. When measuring the content of the residual chlorine in the water samples, the sampling is achieved by adding a certain amount of sample test solution to diffusion layer 5. Left to rest for 10 minutes after sampling, the residual chlorine test strip (paper) is observed for the result. The residual chlorine test strip (paper) is presented with a no color—blue transition, with the visible color boundary A. The value of A is read using the ruler, as shown in (a) of FIG. 3. Alternatively, the similar scanning curve as shown in (b) of FIG. 3 is obtained by the color scanning, and then the value of the inflection point A is read.

Embodiment 8

As shown in FIG. 1, FIG. 3 and FIG. 8, the preparation method for the hydrogen peroxide test strip (paper) based on concentration gradient, used for rapid measurement of the content of hydrogen peroxide in the water samples from different sources, is disclosed. The strip (paper) is composed of five basic functional layers, which are substrate 1, indicator layer 2, reagent layer 3, concentration gradient layer 4 and diffusion layer 5. The multilayer structure is prepared by layer coating. The top layer of the test strip is diffusion layer 5, which is made of the hydrophilic porous cellulose membrane formed by coating. Concentration gradient layer 4 is located under diffusion layer 5, and is made of porous polyvinyl alcohol membrane. The antioxidant (BHT) is first coated on the polyvinyl alcohol porous membrane in a concentration gradient linearly decreasing manner or a concentration gradient exponentially changing manner, and then the reaction solution made of a mixture of 0.037 mol/L citric acid and 0.126 mol/L disodium hydrogen phosphate is coated to prepare concentration gradient layer 4. Reagent layer 3 is located under concentration gradient layer 4, and reagent layer 3 is made of polyvinyl alcohol. The porous membrane is first formed by coating polyvinyl alcohol material, then the reaction solution made of a mixture of 0.05 g/L horseradish peroxidase, 10 g/L trehalose, 5 g/L glycine, 3 g/L BSA and 10 g/L PEG4000 is coated to prepare reagent layer 3. Indicator layer 2 is located under reagent layer 3, and indicator layer 2 is made of a porous polyvinyl alcohol material. The chromogenic agent of indicator layer 2 is 2.0 g/L TMB hydrochloride. Substrate 1 is located under indicator layer 2, and the substrate is made of the colorless transparent PET sheet or the polycarbonate sheet, having a thickness of 0.15-0.2 mm. When measuring the content of the hydrogen peroxide in the water samples, the sampling is achieved by adding a certain amount of biological sample test solution to diffusion layer 5. Left to rest for 10-30 minutes after sampling, the hydrogen peroxide test strip (paper) is observed for the result. The hydrogen peroxide test strip (paper) is presented with a no color—blue transition, with the visible color boundary A. The value of A is read using the ruler, as shown in (a) of FIG. 3. Alternatively, the similar scanning curve as shown in (b) of FIG. 3 is obtained by the color scanning, and then the value of the inflection point A is read.

Embodiment 9

As shown in FIG. 1, FIG. 3 and FIG. 8, the preparation method for the organic phosphorus test strip (paper) based on concentration gradient, used for rapid measurement of the content of the organic phosphorus in the agricultural products, is disclosed. The snip (paper) is composed of five basic functional layers, which are substrate 1, indicator layer 2, reagent layer 3, concentration gradient layer 4 and diffusion layer 5. The multilayer structure is prepared by layer coating. The top layer of the test strip is diffusion layer 5, which is made of the hydrophilic porous cellulose membrane formed by coating. Reagent layer 3 is located under diffusion layer 5, and reagent layer 3 is made of a porous polyvinyl alcohol membrane. The reaction solution made of a mixture of trehalose: 10 g/L, glycine: 5 g/L, BSA: 3 g/L, PEG4000: 10 g/L, citric acid: 0.04 mol/L and disodium hydrogen phosphate: 0.15 mol/L, is coated to prepare reagent layer 3. Concentration gradient layer 4 is located under reagent layer 3, and concentration gradient layer 4 is made of a porous polyvinyl alcohol material. A porous membrane is first formed by uniformly coating the polyvinyl alcohol material the acetylcholinesterase is then coated on the polyvinyl alcohol porous membrane in a concentration gradient linearly decreasing manner or a concentration gradient exponentially changing manner to prepare concentration gradient layer 4. Indicator layer 2 is located under concentration gradient layer 4, and the indicator layer 2 is made of porous polyvinyl alcohol material. The chromogenic agent of indicator layer 2 is 2,6-dichloro-indophenol acetate: 10 g/L. Substrate 1 is located under indicator layer 2, and the substrate is made of the colorless transparent PET sheet or the polycarbonate sheet, having a thickness of 0.15-0.2 mm. When measuring the content of organic phosphorus in the agricultural products, the sampling is achieved by adding a certain amount of biological sample test solution to diffusion layer 5. Left to rest for 10-30 minutes after sampling, the organic phosphorus test strip (paper) is observed for the result. The organic phosphorus test strip (paper) is presented with orange—blue transition, with the visible color boundary A. The value of A is read using the ruler, as shown in (a) of FIG. 3. Alternatively, the similar scanning curve as shown in (c) of FIG. 3 is obtained by the color scanning, and then the value of the inflection point A is read.

Embodiment 10

As shown in FIG. 1, FIG. 3 and FIG. 8, the preparation method for the urea test strip (paper) based on concentration gradient, used for rapid measurement of the content of the urea in the biological samples and water samples from different sources. The strip (paper) is composed of five basic functional layers, which are substrate 1, indicator layer 2, reagent layer 3, concentration gradient layer 4 and diffusion layer 5. The multilayer structure is prepared by layer coating. The top layer of the test strip is diffusion layer 5, which is made of the hydrophilic porous cellulose membrane formed by coating. Reagent layer 3 is located under diffusion layer 5, and reagent layer 3 is made of a porous polyvinyl alcohol membrane. The reaction solution made of a mixture of urease: 20 KU/L, PBS (pH 6.8):5.0 umol/L, trehalose: 1%, glycine: 5 g/L, BSA: 3 g/L, and PEG4000: 10 g/L, is coated to prepare reagent layer 3. Concentration gradient layer 4 is located under reagent layer 3, and concentration gradient layer 4 is made of porous polyvinyl alcohol material. A porous membrane is first formed by uniformly coating the polyvinyl alcohol material and the citric acid is then coated on the polyvinyl alcohol porous membrane in a concentration gradient linearly decreasing manner or a concentration gradient exponentially changing manner to prepare concentration gradient layer 4. Indicator layer 2 is located under concentration gradient layer 4, and the indicator layer 2 is made of a porous polyvinyl alcohol material. The chromogenic agent of indicator layer 2 is bromothymol blue: 1.5%. Substrate 1 is located under indicator layer 2, and the substrate is made of the colorless transparent PET sheet or the polycarbonate sheet, having a thickness of 0.15-0.2 mm. When measuring the content of urea in the blood, the sampling is achieved by adding a certain amount of sample test solution to diffusion layer 5. Left to rest for 30 minutes after sampling, the urea test strip (paper) is observed for the result. The urea test strip (paper) is presented with yellow-blue transition, with the visible color boundary A. The value of A is read using the ruler, as shown in (a) of FIG. 3. Alternatively, the similar scanning curve as shown in (b) of FIG. 3 is obtained by the color scanning, and then the value of the inflection point A is read.

The embodiments above are only illustrative of the technical solutions of the invention, and cannot be explained as limiting the invention. The skilled artisan in the art would appreciate that, without departing from the spirit and scope of the technical solution of the invention, any modifications and equivalents of the invention in any forms or details are within the scope of the invention.

What is claimed is:

1. A dry chemical test strip with multiple layers of membranes based on concentration gradient, comprising: a substrate, an indicator layer, a reagent layer and a diffusion layer which are arranged successively from bottom to top,
    wherein the test strip further comprises a concentration gradient layer, which is arranged on an upper surface or a lower surface of the reagent layer;
    wherein a first reagent, is uniformly applied on the reagent layer, and a second reagent is applied on the concentration gradient layer;
    a concentration gradient $\nabla \rho$ of the second reagent is 0 in a width direction of the test strip, and is a constant or a function of a variable of length in a length direction of the test strip;
    a chromogenic reagent is uniformly applied on the indicator layer.

2. The dry chemical test strip with multiple layers of membranes based on concentration gradient according to claim 1, wherein a material of the concentration gradient layer is any one of polyvinyl alcohol, gelatin and a mixture of the polyvinyl alcohol and the gelatin.

3. The dry chemical test strip with multiple layers of membranes based on concentration gradient according to claim 2, wherein the concentration gradient layer is a porous coating or a prefabricated porous membrane.

4. The dry chemical test strip with multiple layers of membranes based on concentration gradient according to claim 1, wherein the diffusion layer is a hydrophilic membrane.

5. The dry chemical test strip with multiple layers of membranes based on concentration gradient according to claim 4, wherein a siphon structure is provided on the hydrophilic membrane.

6. The dry chemical test strip with multiple layers of membranes based on concentration gradient according to claim 1, wherein the reagent layer is made of a high molecular polymer material.

7. The dry chemical test strip with multiple layers of membranes based on concentration gradient according to claim 6, wherein the reagent layer is a porous coating of a prefabricated porous membrane.

8. The dry chemical test strip with multiple layers of membranes based on concentration gradient according to claim 1, wherein the indicator layer is made of a high molecular polymer material; and the indicator layer is a porous coating or a prefabricated porous membrane.

9. The dry chemical test strip with multiple layers of membranes based on concentration gradient according to claim 1, wherein the substrate is a transparent material, having a thickness of 0.1-0.3 mm.

10. The dry chemical test strip with multiple layers of membranes based concentration gradient according to claim 9, wherein a ruler is provided on a lower surface of the substrate.

* * * * *

UNITED STATES PATENT AND TRADEMARK OFFICE
CERTIFICATE OF CORRECTION

PATENT NO. : 9,664,672 B2
APPLICATION NO. : 15/307009
DATED : May 30, 2017
INVENTOR(S) : Changyun Chen and Rongbin Zeng Page 1 of 1

It is certified that error appears in the above-identified patent and that said Letters Patent is hereby corrected as shown below:

On the Title Page

The (72) INVENTOR(S) should read:
Changyun CHEN; Rongbin ZENG

Signed and Sealed this
Twenty-seventh Day of February, 2018

Andrei Iancu
*Director of the United States Patent and Trademark Office*